(12) United States Patent
Shen

(10) Patent No.: US 6,752,835 B2
(45) Date of Patent: Jun. 22, 2004

(54) TETRAXIAL-LINK ARTIFICIAL LIMB JOINT

(76) Inventor: Hsin Fa Shen, P.O. Box 26-757, Taipei (TW), 106

( * ) Notice: Subject to any disclaimer, the term of this patent is extended or adjusted under 35 U.S.C. 154(b) by 0 days.

(21) Appl. No.: 10/127,156

(22) Filed: Apr. 16, 2002

(65) Prior Publication Data

US 2003/0195637 A1 Oct. 16, 2003

(51) Int. Cl.[7] .................................................. A61F 2/64
(52) U.S. Cl. ....................................................... 623/44
(58) Field of Search .............................. 623/44, 45, 46, 623/43, 42, 39, 27

(56) References Cited

U.S. PATENT DOCUMENTS

| | | | |
|---|---|---|---|
| 2,667,644 A | * | 2/1954 | Johnson ........................ 623/26 |
| 3,820,169 A | * | 6/1974 | Long et al. .................... 623/39 |
| 3,934,273 A | * | 1/1976 | Mortensen .................... 623/44 |
| 4,145,766 A | * | 3/1979 | May .............................. 623/45 |
| 4,215,441 A | * | 8/1980 | Wilson .......................... 623/31 |
| 4,310,932 A | * | 1/1982 | Nader et al. .................. 623/39 |
| 4,549,318 A | * | 10/1985 | Takahama ..................... 623/44 |
| 5,800,565 A | * | 9/1998 | Biedermann ................. 623/38 |
| 5,921,358 A | * | 7/1999 | Gramnas ..................... 188/294 |
| 5,948,021 A | * | 9/1999 | Radcliffe ...................... 623/44 |
| 6,086,616 A | * | 7/2000 | Okuda et al. ................. 623/44 |
| 6,322,594 B1 | * | 11/2001 | Boiten et al. ................. 623/27 |
| 2002/0177905 A1 | * | 11/2002 | Yih et al. ...................... 623/24 |

* cited by examiner

*Primary Examiner*—Corrine McDermott
*Assistant Examiner*—Alvin Stewart
(74) *Attorney, Agent, or Firm*—Cohen, Pontani, Lieberman & Pavane

(57) ABSTRACT

A tetraxial-link artificial limb joint includes a kneecap, front connection boards, a rear connection rod, a first axis, a second axis, a third axis, a fourth axis, and a shank connection seat. The point for force acting is below these four axes, thereby forming an inverse triangular therebetween. The inverse triangular is maintained to not bend the artificial limb joint until the user's forefoot land down again for each step.

3 Claims, 6 Drawing Sheets

TETRAXIAL-LINK ARTIFICIAL LIMB JOINT

BACKGROUND OF THE INVENTION

1. Field of the Invention

The present invention relates to a tetraxial-link artificial limb joint and, more particularly, to a tetraxial-link artificial limb joint enhancing the convenience and safety for the handicapped while they walk.

2. Description of Prior Arts

Along with continual progress of present medical techniques, not only remedial effects have been improved, but also beneficial rehabilitations are highly required. Many handicapped can depend on the transplantation or artificial limbs for the purpose of rehabilitation. Among the transplantation and artificial limbs, the latter are much more common while applied to the handicapped because they can facilitate the action of the handicapped, and further make up physical and mental trauma of the handicapped.

As shown in FIG. 1, in a conventional artificial limb joint 10, a virtual point 102 for force acting is above the kneecap, meaning that the handicapped have to control this kind of artificial limb through their stumps. Based on the FIG. 1, it is very clear that the virtual point 102 for force acting and other joints of prior art artificial limb distribute in an uphill triangular manner.

Because the virtual point 102 of the link 101 is above the kneecap, the artificial limb joint 10 can be easily bent. However, the handicapped may easily stumble when walking. Further, the handicapped are inferior in physical strength and reaction to properly maneuver this artificial limb. Therefore, the artificial limb joint 10 with the uphill triangular distribution for the force controlling point and other joints is very likely risky for the handicapped.

Accordingly, the above artificial limb joint has inconvenience and drawbacks in practical use. The present invention aims to resolve the problems in the prior art.

SUMMARY OF THE INVENTION

The primary objective of the present invention is to provide a tetraxial-link artificial limb joint whose axes and the virtual point for force acting are distributed in an inverse triangular manner. The virtual point is below the shank joint seat of the artificial limb, so that not controlled by the stump, but by the consequent variation of center of gravity and the displacement of pivot point below the shank when one handicapped walks. As this result, spiritual and physical burden of the handicapped can be effectively lessened to enhance reliability and safety of the artificial limb joint so that novices can quickly adapt to the artificial limb based on the present invention.

To achieve the above object, the present invention provides a tetraxial-link artificial limb joint having a kneecap, front connection boards, a rear connection rod, a first axis, a second axis, a third axis, a fourth axis, and a shank connection seat. A first pivotal portion and a second pivotal portion are alternately disposed on the kneecap. The first pivotal portion is pivotally joined with the top end of the front connection boards by the first axis. The second pivotal portion is pivotally joined with the upper portion of the rear connection rod by the second axis. The lower portion of the rear connection rod is clamped to and pivotally joined with the upper end of the shank connection seat by the third axis. The lower portion of the front side of the shank connection seat is pivotally joined with the bottom end of the front connection boards by the fourth axis. Dependent upon the above configuration, the user drives the artificial limb through the irtual point for force acting, which locates away from four axes to form a virtually inverse triangle therebetween.

The various objects and advantages of the present invention will be more readily understood from the following detailed description when read in conjunction with the appended drawing, in which:

DETAILED DESCRIPTION OF THE PREFERRED EMBODIMENT

Figure 1:
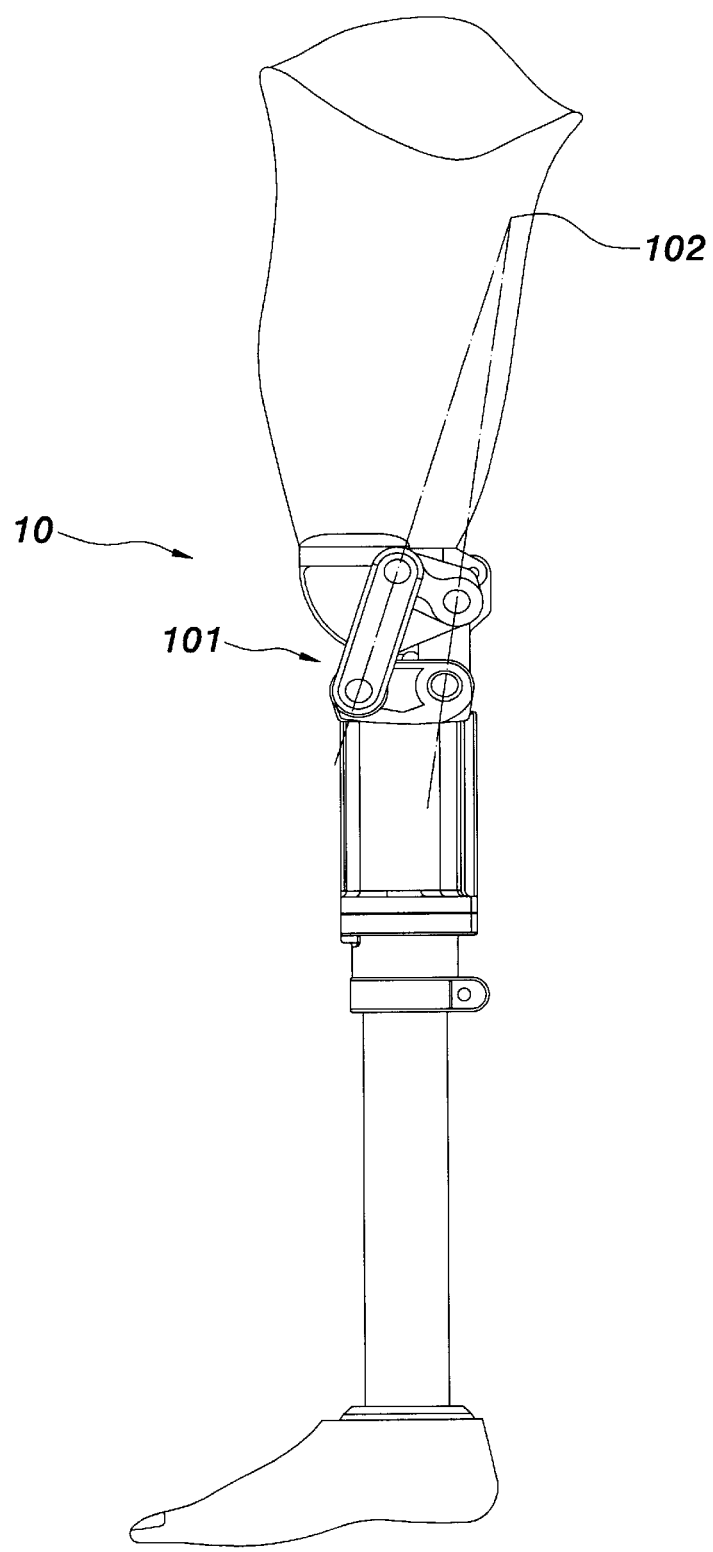
FIG. 1 is a schematic diagram of showing a prior art artificial limb joint while used.
Figure 2:
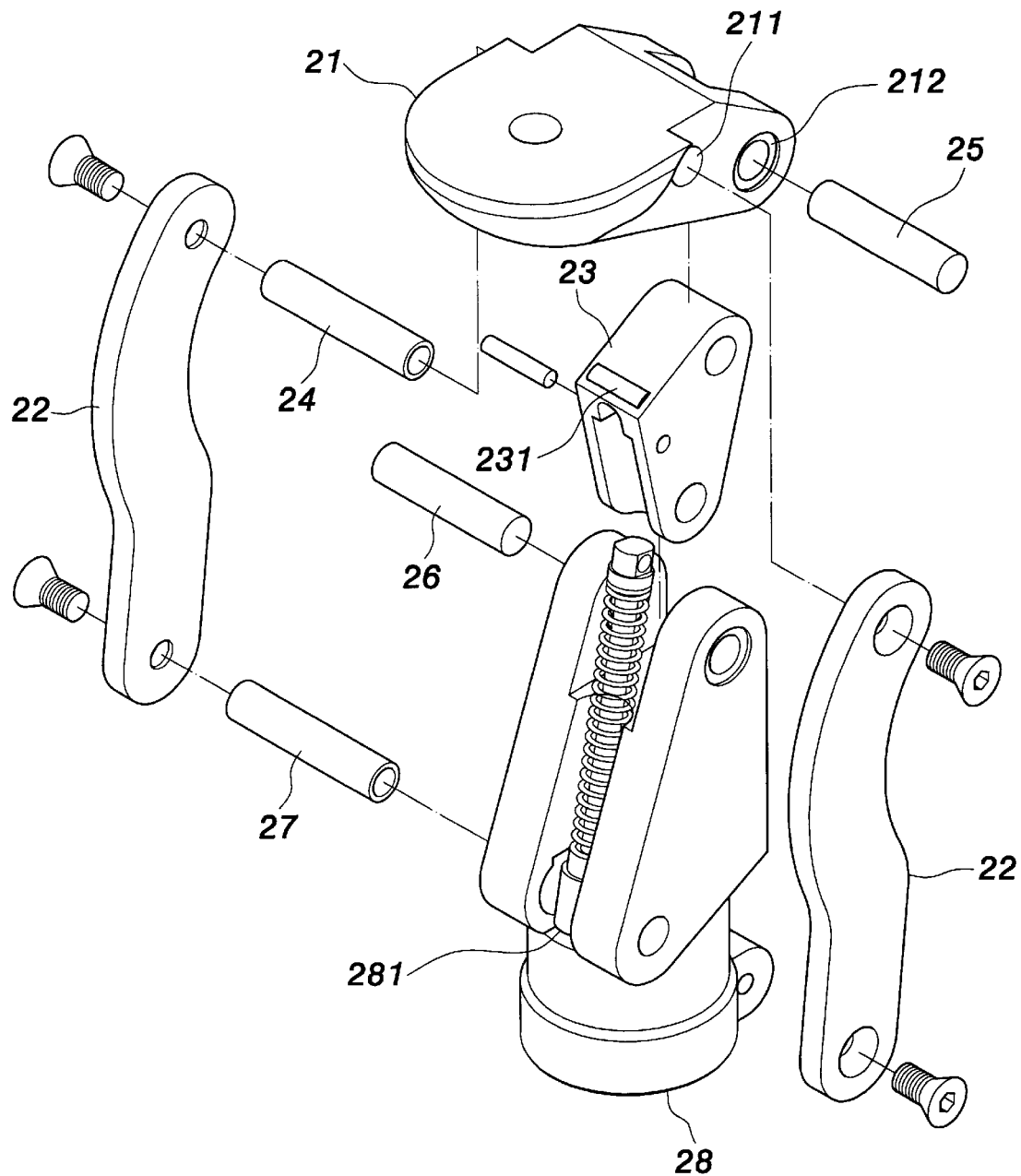
FIG. 2 is an exploded perspective view of the present invention.
Figure 3:
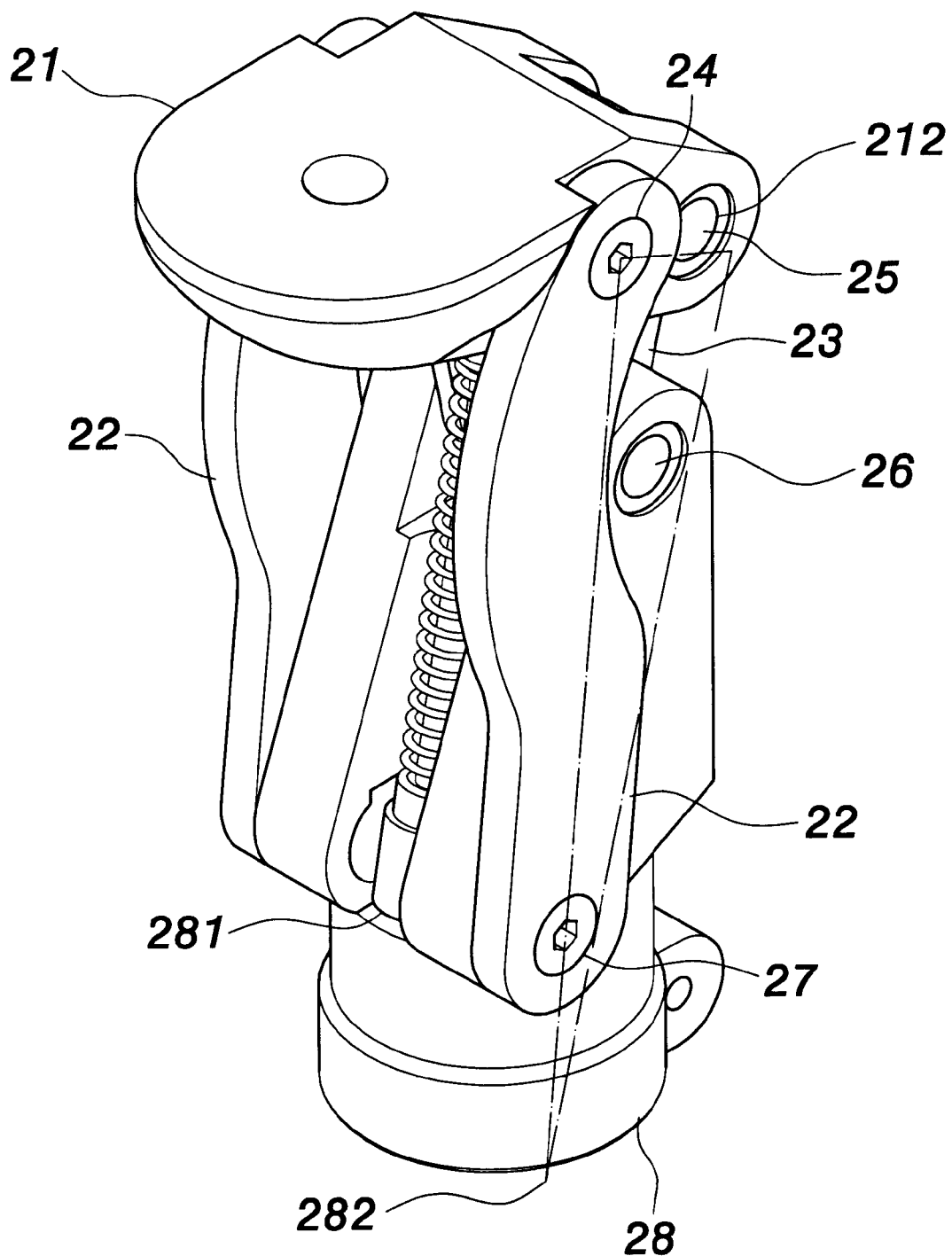
FIG. 3 is a perspective assembly view of the present invention.

As shown in FIGS. 2 and 3, the present invention relates to a tetraxial-link artificial limb joint having a kneecap 21, front connection boards 22, a rear connection rod 23, a first axis 24, a second axis 25, a third axis 26, a fourth axis 27, and a shank connection seat 28.

A first pivotal portion 211 and a second pivotal portion 212 are alternately disposed on the kneecap 20. The first pivotal portion 211 is pivotally joined with the top end of the front connection boards 22 by the first axis 24. The second pivotal portion 212 is pivotally joined with the upper portion of the rear connection rod 23 by the second axis 25. A buffer element 231 disposed at one side of the upper portion of the rear connection rod 23 is to reduce impact of the interaction between the connection rod 23 and kneecap 21. The lower portion of the rear connection rod 23 is clamped to and pivotally joined with the upper end of the shank connection seat 28 by the third axis 26. An elastic rod body 281 is fixedly disposed within the shank connection seat 28 to help the artificial limb stretch and restore, back and forth. The lower portion of the front side of the shank connection seat 28 is pivotally joined with the bottom end of the front connection boards 22 by the fourth axis 27. A virtual point 282 for force acting is formed below the four axes 24, 25, 26, and 27, all of which form an inverse triangle, as shown in FIG. 4.

Figure 4A:
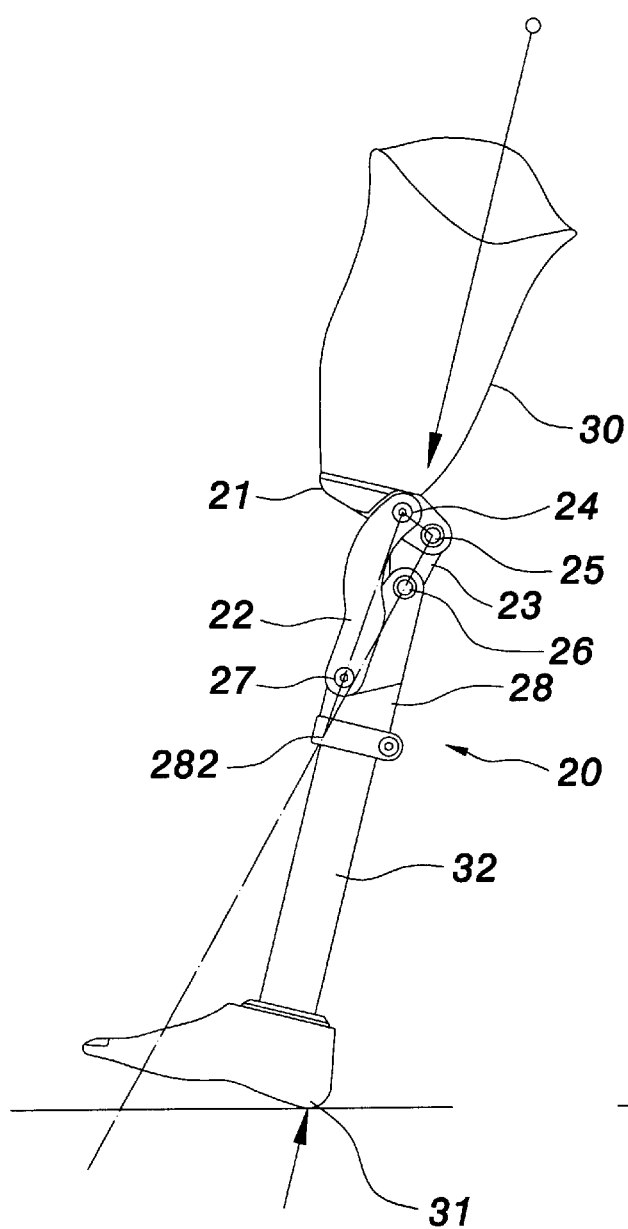
FIG. 4A is a schematic diagram of showing an operation state for the present invention.

As shown in FIG. 4A, when the user strides forward, the four axes 24, 25, 26, and 27, supporting each other at this point, form an inverse triangle therebetween. At the present time, no matter how much force is exerted by the user, the artificial limb joint 20 will not bend because the artificial limb joint 20 is stretching.

Figure 4B:
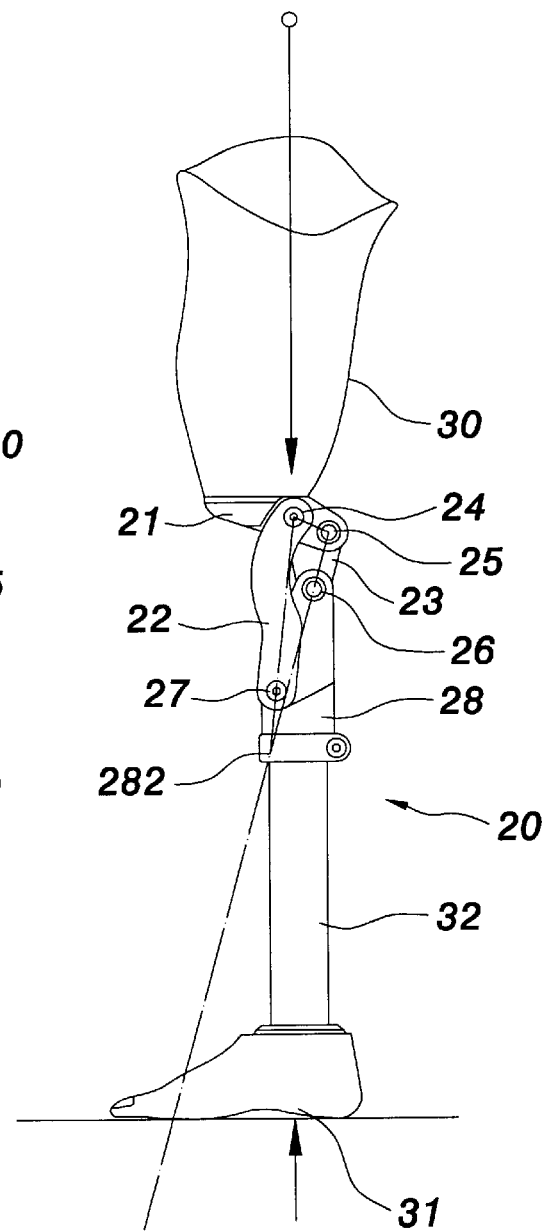
FIG. 4B shows another operation state of the present invention.

As shown in FIG. 4B, when the artificial limb joint 20 lands down, the four axes 24, 25, 26, and 27 also form an inverse triangular and each of them supports each other, thus not bending the artificial limb joint 20.

Figure 4C:
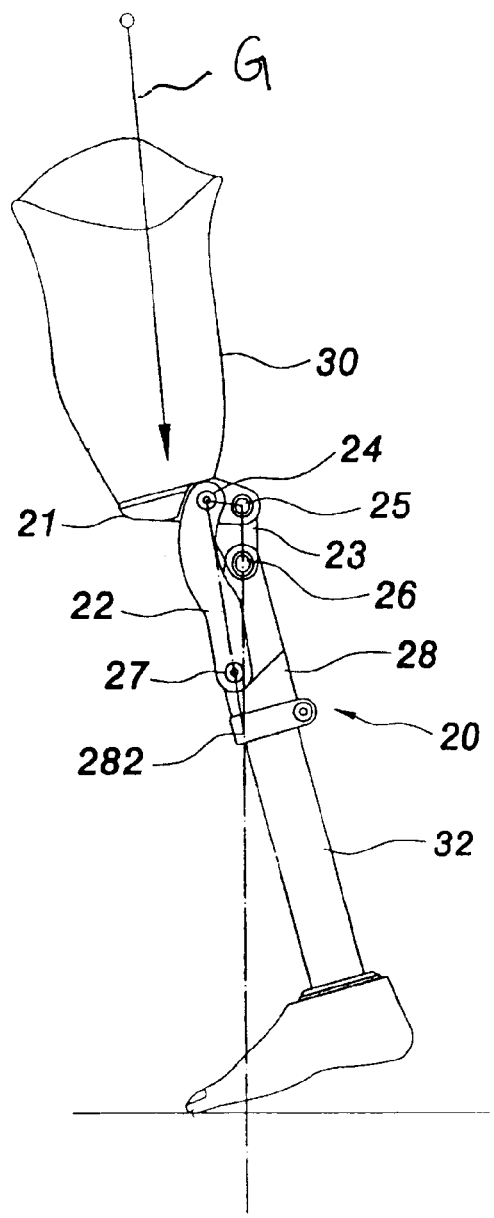
FIG. 4C shows another operation state of the present invention.

As shown in FIG. 4C, when the user's body leans forwards, the whole artificial limb joint 20 is behind the center of gravity G of the user. Consequently, the original inverse triangular support of the four axes 24, 25, 26, and 27 does not exist anymore, thus allowing the artificial limb joint 20 to bend (FIG. 4D).

Figure 4D:
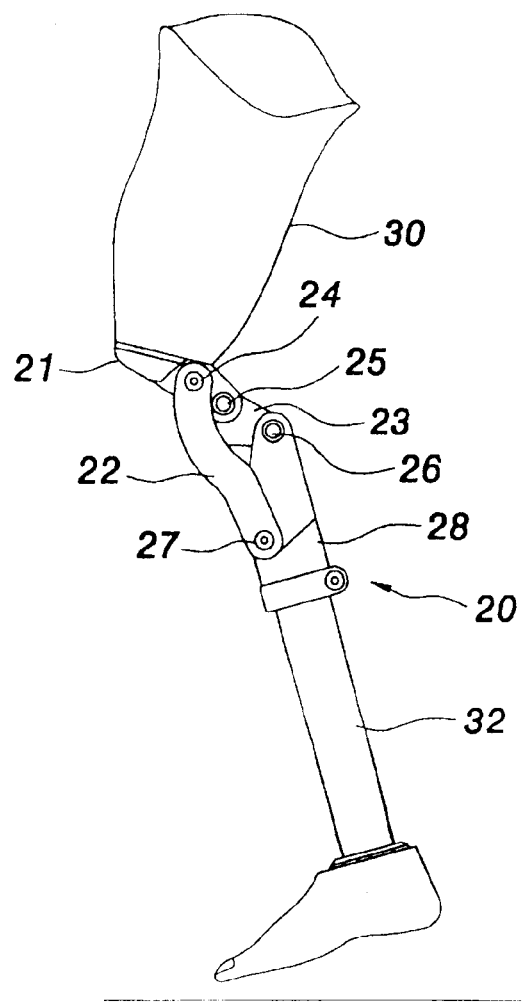
FIG. 4D shows another operation state of the present invention.

As shown in FIG. 4D, when the user moves the stump 30 forward to consequently move the artificial limb joint 20 forward also, the artificial limb joint 20 will be in a suspension state.

Figure 4E:
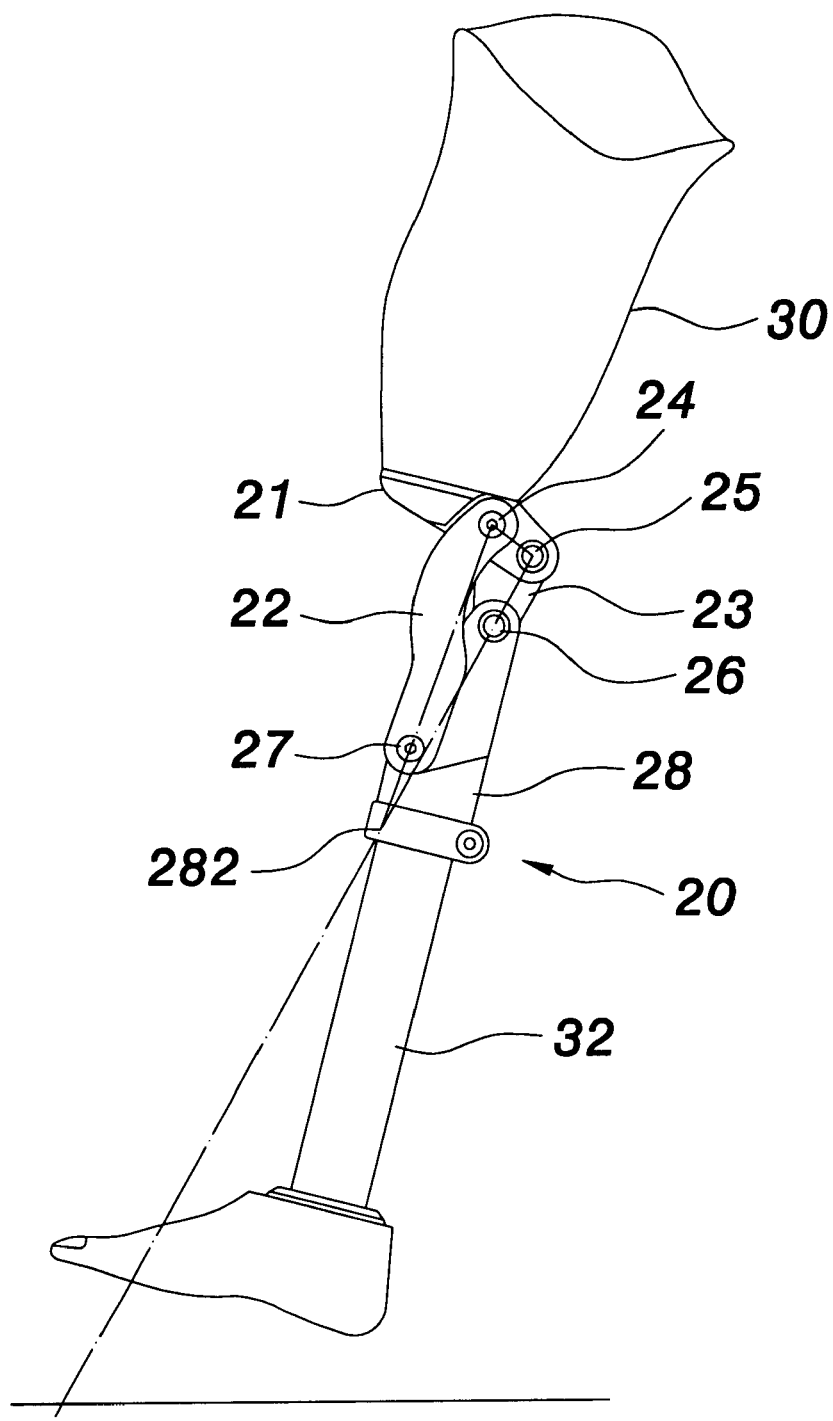
FIG. 4E still shows another operation state of the present invention.

As shown in FIG. 4E, when the artificial limb joint 20 kicks forward to stretch and prepares to land on the ground again, because the artificial limb joint 20 is in stretch, the aforementioned inverse triangle therebetween restores again, thereby not bending by the weight of shank skeleton 32 or the force exerted by gravity. Thus, there is no risk of a downward bend or a rearward bend, so that no matter how long the artificial limb joint 20 does not touch down, the artificial limb joint 20 will be more firmly retained because of the mutual inverse triangular support of the four axes 24, 25, 16, and 27 and the counterforce caused by the weight of the shank skeleton 32.

Although the present invention has been described with reference to the preferred embodiment thereof, it will be understood that the invention is not limited to the details thereof. Various substitutions and modifications have been suggested in the foregoing description, and other will occur to those of ordinary skill in the art. Therefore, all such substitutions and modifications are intended to be embraced within the scope of the invention as defined in the appended claims.

I claim:

1. A tetraxial-link artificial limb joint having four axes comprising: a kneecap, a top end and a front connection board, an upper portion and a lower portion of a rear connection rod, and an upper end and a lower portion of a front side of a shank connection seat, and forming a virtual point for force acting below the four axes, and wherein the virtual point for force acting and four axes form a virtual inverse triangle therebetween.

2. The tetraxial-link artificial limb joint as claimed in claim 1, further comprising a buffer element disposed at one side of an upper portion of said rear connection rod.

3. The tetraxial-link artificial limb joint as claimed in claim 1, where the shank connection seat further comprises an elastic rod body fixedly disposed therewithin.

* * * * *